(12) United States Patent
Benedict et al.

(10) Patent No.: US 6,753,319 B2
(45) Date of Patent: Jun. 22, 2004

(54) D-MANNOSE CONTRACEPTIVES

(75) Inventors: Dale L. Benedict, Fayetteville, AR (US); Martha Benedict, Fayetteville, AR (US)

(73) Assignee: BioTech Pharmacal, Inc., Fayetteville, AR (US)

( * ) Notice: Subject to any disclaimer, the term of this patent is extended or adjusted under 35 U.S.C. 154(b) by 0 days.

(21) Appl. No.: 10/231,399

(22) Filed: Aug. 29, 2002

(65) Prior Publication Data

US 2003/0073643 A1 Apr. 17, 2003

Related U.S. Application Data

(60) Provisional application No. 60/315,661, filed on Aug. 29, 2001.

(51) Int. Cl.[7] .................................................. A61K 31/70

(52) U.S. Cl. ............................ 514/35; 514/23; 514/843

(58) Field of Search ............................ 514/35, 23, 843

(56) References Cited

U.S. PATENT DOCUMENTS

| | | |
|---|---|---|
| 5,854,254 A | 12/1998 | Benoff |
| 5,939,279 A | 8/1999 | Smith et al. |
| 5,994,086 A | 11/1999 | Benoff |

OTHER PUBLICATIONS

H. R. Morris et al., "Gender–Specific Glycosylation of Human Glycodelin Affects Its Contraceptive Activity," *The Journal of Biological Chemistry*, vol. 271, No. 50, Dec.13, pp. 32159–32167.
Aanesen, et al, "Evidence for gamma–aminobutyric acid specific binding sites on human spermatozoa," abstract only, Jul. 1995, 1885–90, *Hum Reprod*.
Barros, et al, "Early steps of sperm–egg interactions during mammalian fertilization." abstract only, Jan. 1996, 33–9, *Cell Biol Int*.
Batova, et al, "Human sperm surface glycoprutein involved in sperm–zona pellucide interaction," abstract only, Jun. 1998, 1275–1287, *Int J Androl*.
Bedford, "Mammalian fertilization misread? Sperm penetration of the eutherian zona pellucida is unlikely to be a lytic event," 1998, 1275–1287, *Biology of Reproduction*.
Bedford, "The contraceptive potential of fertilization: a physiological perspective." abstract only, May 1994, 842–58, *Hum Reprod*.
Benoff, et al, "Human sperm fertilizing potential in vitro is correlated with differential expression of a head–specific mannose–ligand receptor." abstract only, Apr. 1993, 854–62, *Fertility and Sterility*.
Benoff, et al, "Fertilization potential in vitro is correlated with head–specific mannose–ligand receptor expression, acrosome status and membrane cholesterol content." abstract only, Dec. 1993, 2155–66, *Hum Reprod*.
Benoff, et al, "Head–specific mannose–ligand receptor expression in human spermatozoa is dependent on capacitation–associated membrane cholesterol loss,." abstract only, Dec. 1993, 2141–54, *Hum Reprod*.
Benoff, et al, "Induction of the human sperm acrosome reaction with mannose–containing neoglycoprotein ligands." abstract only, Oct. 1997, 827–37, *Molecular Human Reprod*.
Blackmor, Eisoldt "The neoglycoprotein mannose–bovine serum albumin, but not progesterone, activates T–type calcium channels in human spermatozoa." abstract only, Jun. 1999, 498–506, *Molecular Human Reprod*.
Chen et al, "Expression of mannose–binding sites on human Apermatozoa and their role in sperm–zona pellucida binding." abstract only, Jan.–Feb. 1995, 55–63, *J Androl*.
Clark, et al, "New concepts in human sperm–zona pellucida interaction." abstract only, Oct. 1995, Suppl 31–7, *Hum Reprod*.
Cornwall, et al, "Inhibition of the mouse sperm surface alpha–D–mannosidase inhibits sperm–egg binding in vitro." abstract only, May 1991, 913–21, *Biol Reprod*.
Crozet, "Acrosome reaction and fertilization." abstract only, May 1994, 328–30, *Contracept Fertil Sex*.
Franken, "New aspects of sperm–zona pellucida binding," abstract only, Aug.–Sep. 1998, 263–8, *Andrologi*.
Franken, et al, "Inhibition of G protein in human sperm and its influence on acrosome reaction and zona pellucida binding." abstract only, Dec. 1996, 1009–11, *Fertil Steril*.
Fraser, "Sperm capacitation and the acrosome reaction." abs only, Apr. 1998, Suppl I:9–19, *Hum Reprod*.
Fraser, "p–Aminobenzamidine, an acrosin inhibitor inhibits mouse sperm penetration of the zone pellucida but not the acrosome raction." abstract only, May 1982, 185–94, *J Reprod Fertil*.
Gabriele, et al, "Carbohydrate binding activity in human spermatozoa: localization, specificity, and involvement in sperm–egg fusion." abstract only, Jun. 1998, 543–53, *Mol Hum Reprod*.
Garrett, et al, "Selectivity of the human sperm–zona pellucida binding process to sperm head morphometry." abstract only, Feb. 1997, 362–71, *Fertil Steril*.

(List continued on next page.)

*Primary Examiner*—Donna Jagoe
(74) *Attorney, Agent, or Firm*—Jackson Walker, LLP; Mark H. Miller; William B. Nash

(57) ABSTRACT

The present invention concerns the use of D-Mannose to prevent or inhibit uniting of sperm and egg in the conception process. The administration of D-Mannose to a female such that the environment of an egg has sufficient D-Mannose to inhibit interaction of sperm and the egg and prevent or inhibit conception. D-Mannose dosages may be complimentary to other methods of birth control to enhance their effectiveness.

1 Claim, No Drawings

OTHER PUBLICATIONS

Gheri, et al, "Lectin binding in the human endometrium in early luteal phase following controlled ovarian hyperstimulation." abstract only, Jul. 1998, 737–42, *Histol Histopathol.*

Holden et al, "Assessment of the human sperm acrosome reaction using concanavalin A lectin." abstract only, Mar. 1990, 247–57, *Molecular Reproduction and Development.*

Kaskar, et al, "The relationship between morphology, motility and zona pellucida binding potential of human spermatozoa." abstract only, Jan.–Feb. 1994, 1–4, *Andologia.*

Kuroda, et al, "Quantitative assessment of human sperm acrosome reaction by using fluorescein isothiocyanate conjugated concanavalin A–comparison between highly purified acrosome reacted with non–acrosome reacted sperm.", May–Jun. 1998, 215–24, *Arch Androl.*

Liu, et al, "Disordered acrosome reaction of spermatozoa bound to the zona pellucida: a newly discovered sperm defect causing infertility with reduced sperm–zona pellucida penetration and reduced fertilization in vitro." abstract only, Sep. 1994, 1694–700, *Hum Reprod.*

Loeser, Tulsiani, "The role of carbohydrates in the induction of the acrosome reaction in mouse spermatozoa." abstract only, Jan. 1999, 94–101, *Biol Reprod.*

Miranda et al, "Glycosidic residues involved in human sperm–zona pellucida binding in vitro." abstract only, May 1997, 399–404, *Molecular Human Reprod.*

Monga, Roberts, "Spermagglutination by bacteria: receptor–specific interactions." abstract only, Mar.–Apr. 1994, 151–6, *J Andrology.*

Morales, et al, "Sperm–oocyte interaction: studies on the kinetics of zona pellucida binding and acrosome reaction of human spermatozoa." abstract only, May–Jun. 1994, 131–7, *Andrologia.*

Mori, et al, "Blocking of human fertilization of carbohydrates." abstract only, Oct. 1993, 1729–32, *Hum Reprod.*

Mori, et al, "Significance of D–mannose as a sperm receptor site on the zona pellucida in human fertilization." abstract only, Jul. 1989, 207–11, *Am J Obstet Gynecol.*

Niwa, Iritani, "Effect of various hexoses on sperm capacitation and penetration of rat eggs in vitro." abstract only, Jul. 1978, 267–71, *J Reprod Fertil.*

Ou, "Acrosome reaction in the head–attached human sperm." abstract only, Jan.–Feb. 1994, 17–20, *Andrologia.*

Philip, et al, "Charge interactions in sperm–egg recognition." abstract only, Nov. 1997, 401–10, *Acta Histochemica.*

Revah, et al, "Physiological state of bull sperm affects fucose and mannose–binding properties." abstract only, Apr. 2000, 1010–5, *Biol Reprod.*

Shalgi, et al, "The role of carbohydrate residues in mamm–aian fertilization." abstract only, Jul. 1997, 813–22, *Histol Histopathol.*

Shalgi, et al, "The role of carbohydrates in sperm–egg interactions in rats." abstract only, Apr. 1986, 446–52, *Biol Reprod.*

Sinowatz, et al, "Protein–carbohydrate interactions during fertilization." abstract only, 1998, 196–205, *Acta Anat.*

Son, et al, "Acrosome reaction of human spermatozoa is mainly mediated by alph1H T–type calcium channels." abstract only, Oct. 2000, 893–7, *Mol Hum Reprod.*

Tesarik, et al, "Expression of D–mannose binding sites on human spermatozoa: comparison of fertile donors and infertile patients." abstract only, Jul. 1991, 113–8, *Fertil Steril.*

Topfer–Petersen, "Carbohydrate–based interactions on the route of a spermatozoon to fertilization." abstract only, Jul.–Aug. 1999, 314–329, *Hum Reprod Update.*

Topfer–Petersen et al, "Oocyte–sperm interactions." abstract only, Jul. 2000, 653–62, *Anim Reprod Sci.*

Wassar–man, "Role of carbohydrates in receptor–mediated fertilization in mammals." abstract only, 1989, 135–49, *Ciba Found Symp.*

Wassar–man, "Towards molecular mechanisms for gamete adhesion and fusion during mammalian fertilization." abstract only, Oct. 1995, 658–64, *Curr Opin Cell Biol.*

Wolff, et al, "Adherence of Escherichia coli tp sperm: a Mannose mediated phenomenon leading to agglutination of sperm and E. coli." abstract only, Jul. 1993, 154–8, *Fertil Steril.*

Yogev, et al, "Correlation between sperm penetration into the human zona pellucida and in vitro fertilizaition rates." abstract only Mar.–Apr. 1997, 71–5, *Andrologia.*

Yoshida–Momiya, et al, "Mannose–binding molecules of rat spermatozoa and sperm–egg interaction." abstract only, Nov. 1999, 335–46, *Zygote.*

Youssef, et al, "Effect of sperm viability, plasmalemma integrity, and capacitation on patterns of expression of mannose–binding sites on human sperm." abstract only, Jan.–Feb. 1997, 67–74, *Arch Androl.*

Youssef, et al, "Mannose–binding sites on human spermatozoa and sperm morphology." abstract only, Oct. 1996, 640–5, *Fertil Steril.*

Zara, Naz, "The role of carbohydrates in mammalian sperm–egg interactions: how important are carbohydrate epitopes?" Oct 1, 1998, 1028–1038, *Frontiers In Bioscience 3.*

D-MANNOSE CONTRACEPTIVES

This application claims priority under 35 U.S.C. Section 119(e) to U.S. Provisional Application Serial No. 60/315,661, filed Aug. 29, 2001.

FIELD OF THE INVENTION

The present invention relates to the use of D-Mannose to inhibit or prevent the uniting of a sperm and egg in conception. The presence of excess mannose in a reproductive system inhibits sperm capacitation.

BACKGROUND OF THE INVENTION

The search for effective contraceptives that are both inexpensive and without undesired side effects has been a long standing activity. It has been noted that there is a D-Mannose binding constituent of human sperm surfaces. It has also been shown that D-Mannose is very useful in alleviation of the urinary tract, infection and cystitis. The present invention concerns the use of D-Mannose administration to a woman as a method of inhibiting conception.

DESCRIPTION OF PREFERRED EMBODIMENT

D-Mannose has been widely used in the feed industry to treat and prevent urinary tract infections by inhibiting the adherence of bacteria to membranes or cell walls. Interactions between proteins and D-Mannose in the acrosome of mice, rats, horses chickens humans and other animals, appear to be related to adherence of the sperm to the egg. Various studies have been performed, some indicating that D-Mannose causes greater adherence of sperm acrosome to eggs and others that it causes less adherence. In any case, the present invention involves the inhibition of conception while also preventing or alleviating urinary tract infections or cystitis.

It is understood that a certain amount of silica is well known to those skilled in the art to prevent D-Mannose from compacting upon exposure to moisture. Thus silica is useful to mix with D-Mannose powder prior to encapsulation.

It has been noticed that equine artificial insemination often results in endometriosis which is a painful infection of the uterus. To protect against infection, the equine sperm was placed in a mannose solution. While infection was avoided, it was also observed that conception did not occur in the treated animals. D-Mannose in sufficient quantities at the appropriate times appears to prevent conception (at least sometimes) by inhibiting the sperm from adhering or attaching to the egg via acrosome of the sperm. In one preferred embodiment the present invention involves oral administration, preferably in capsule form, of D-Mannose to a female with the possibility of sexual intercourse in the near future. One preferable dosage for an average adult female human would involve the ingestion of about three (3) capsules, each containing about 420 milligrams of D-Mannose about every two (2) hours beginning about a day before intercourse. This may be reduced to about 2–3 of such capsules about one hour before intercourse and about the same dosage about one hour after. The oral spray of a D-Mannose solution may also be used. Such dosages and timing may vary to a significant extent to be most effective. The useful dose for an average adult female human would range from about 1 gram to about 10 grams of D-Mannose per day. Useful doses for other animals can be determined by scaling the relative to the other animal's weight relative to average adult female humans. The administration of D-Mannose to domestic or wild animals may be done to inhibit animal population growth. Such administration may be in water, salt or foods.

The inventor envisions soft drinks or alcohol-containing beverages supplemented with D-Mannose and useful to lessen the possibility of conception.

While capsules are preferred at the present time, it is conceivable that D-Mannose may be utilized simply as a powder addition to drinks or foods. The dosages could be supplemented or replaced by a mannose-containing contraceptive jelly, douche or intravaginal cream, or the like. What is important is for the subject woman to gain an internal concentration of mannose efficient to inhibit the fertilizing interaction of sperm with the egg.

While the exact mechanism of this contraceptive effect is incompletely defined, it is not essential to the understanding or use of the present invention. The present invention, involves the successful inhibition of sperm-egg interaction to prevent or reduce the likelihood of conception by the presence of a sufficient quality of D-Mannose. It is believed that D-Mannose binds to sites on the sperm which are used by the sperm in its interaction with the egg in a way in which common table sugar, sucrose, and most other commonly used sugars do not. While D-Mannose is most preferably used in capsules, tablets or powders may also be used. Douches containing D-Mannose may be used alone or in combination with oral D-Mannose to inhibit effective sperm egg interaction. D-Mannose dosages are also usable to enhance the effectiveness of other contraceptive methods such as condoms, diaphragms, hormonal pills, etc. D-Mannose may be supplied vaginally with a diaphragm, or a condom that contains D-Mannose. It may be supplied taken with separate hormonal pills or in pills which are combined with hormonal pills. D-Mannose douches or intervaginal creams are effective means of delivering the D-Mannose particularly if used within one day before or soon after intercourse. The closer in time to the intercourse the vaginal applications are made, the more effective the application. Women of child-bearing/age not desiring to become pregnant should take a constant maintenance dose of D-Mannose.

Because the D-Mannose binds to sperm in a manner which, at some concentration, makes the sperm less efficient in penetrating the egg, there is a synergistic interaction with other contraceptive applications which also prevent conception by preventing sperm from penetrating the egg.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

What is claimed:

1. A method for inhibiting conception comprising administering D-Mannose to a female in an amount effective to inhibit interaction between a sperm and an egg of said female wherein said D-Mannose is administered in the form of a capsule or tablet, said D-Mannose is administered within one day prior to or one day after sexual intercourse and wherein the administration is by means of the female ingesting about three capsules, each capsule containing about 420 milligrams of D-Mannose about every two hours beginning about a day before said intercourse, ingestion being reduced to two or three of such capsules about one hour before intercourse and about the same dosage about one hour thereafter.

* * * * *